United States Patent [19]

Rada

[11] Patent Number: 4,695,339
[45] Date of Patent: Sep. 22, 1987

[54] METHOD FOR PREPARING TISSUE SECTIONS

[76] Inventor: David C. Rada, 6347 Outlook, Mission, Kans. 66202

[21] Appl. No.: 914,814

[22] Filed: Oct. 3, 1986

[51] Int. Cl.$^4$ ............................................. B32B 35/00
[52] U.S. Cl. ...................................... 156/80; 156/57; 156/241; 156/285; 156/289; 156/298; 156/344; 83/915.5; 269/21
[58] Field of Search ................. 269/21; 83/915.5, 170, 83/15; 156/80, 57, 379, 241, 344, 285–286, 108, 152, 242, 248, 250, 289, 298, 299, 381–382, 498, 510, 556

[56] References Cited

U.S. PATENT DOCUMENTS

| | | |
|---|---|---|
| 3,218,896 | 11/1965 | McCormick . |
| 3,520,055 | 7/1970 | Jannett ................................. 269/21 |
| 3,598,006 | 8/1971 | Gerber ................................. 269/21 |
| 3,654,019 | 4/1972 | Cusik ................................. 156/285 |
| 3,667,330 | 6/1972 | Kobernick . |
| 3,737,335 | 6/1973 | Feinberg ............................... 156/57 |
| 3,742,802 | 7/1973 | Maerz ................................... 269/21 |
| 3,765,289 | 10/1973 | Gerber ................................. 269/21 |
| 3,803,958 | 4/1974 | Fernandez-Moran . |
| 3,832,923 | 9/1974 | Lassmann et al. . |
| 4,012,475 | 3/1977 | Kindel . |
| 4,060,440 | 11/1977 | Behme ................................ 83/915.5 |
| 4,190,472 | 2/1980 | Slonicki ................................ 156/57 |
| 4,532,838 | 8/1985 | Söderkvist . |
| 4,543,862 | 10/1985 | Levene ................................. 269/21 |
| 4,545,831 | 10/1985 | Ornstein ............................... 156/57 |

OTHER PUBLICATIONS

Conception "How to Prepare Tissue Blocks" (published as Letter to the Editor), J. Dermatol. Surg. Oncol., vol. 12, No. 2, Feb. 1986, pp. 112, 113.
Picoto "Technical Procedures for Mohs Fresh Tissue Surgery", J. Dermatol. Surg. Oncol., vol. 12, No. 2, Feb. 1986, pp. 134–138.
Hanke et al., "Chemosurgical Reports: Frozen-Section Processing with the Miami Special"; J. Dermatol. Surg. Oncol., vol. 9, No. 4, Apr. 1983, pp. 260–262.
Swanson "Mohs Surgery"; Arch. Dermatol., vol. 119, Sep. 1983, pp. 761–772.
Carter "A New Method for Preparing Tissue Blocks for Cryostat Sectioning"; J. Dermatol. Surg. Oncol., vol. 11, No. 7, Jul. 1985, pp. 687–689.

Primary Examiner—Donald E. Czaja
Assistant Examiner—Merrell C. Cashion, Jr.
Attorney, Agent, or Firm—Litman, McMahon and Brown

[57] ABSTRACT

A system for preparing tissue blocks for sectioning in a microtome is provided. A vacuum-retracted membrane of plastic film material is used to draw a tissue block or specimen into planar contact with a polished platform that is positioned in a vacuum receptacle assembly. A cover plate forms a seal between the membrane and the vacuum receptacle assembly, whereupon a vacuum source is activated to retract the membrane against the tissue block and polished platform. The user adjusts any peripheral edges of the tissue block that are not properly oriented or in a planar position. The tissue block is frozen to the platform once it is properly oriented. The membrane is subsequently peeled away from the platform and the platform/block complex is placed into a mounting device and O.C.T. compound is applied thereto. The O.C.T. compound is also applied to a corrugated platform carried by the mounting device, and the polished and corrugated platforms are mated, with the O.C.T. compound and tissue block therebetween. The O.C.T. compound is allowed to solidify, and the platforms are separated, with the tissue block being retained by the corrugated platform. The tissue specimen is ready for sectioning as part of the Mohs fresh tissue surgical technique.

3 Claims, 11 Drawing Figures

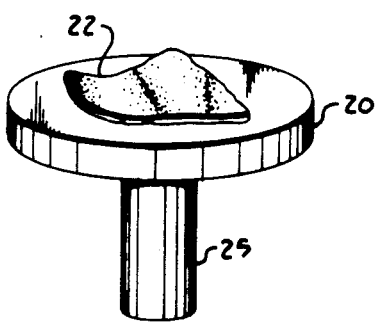
Fig. 3.
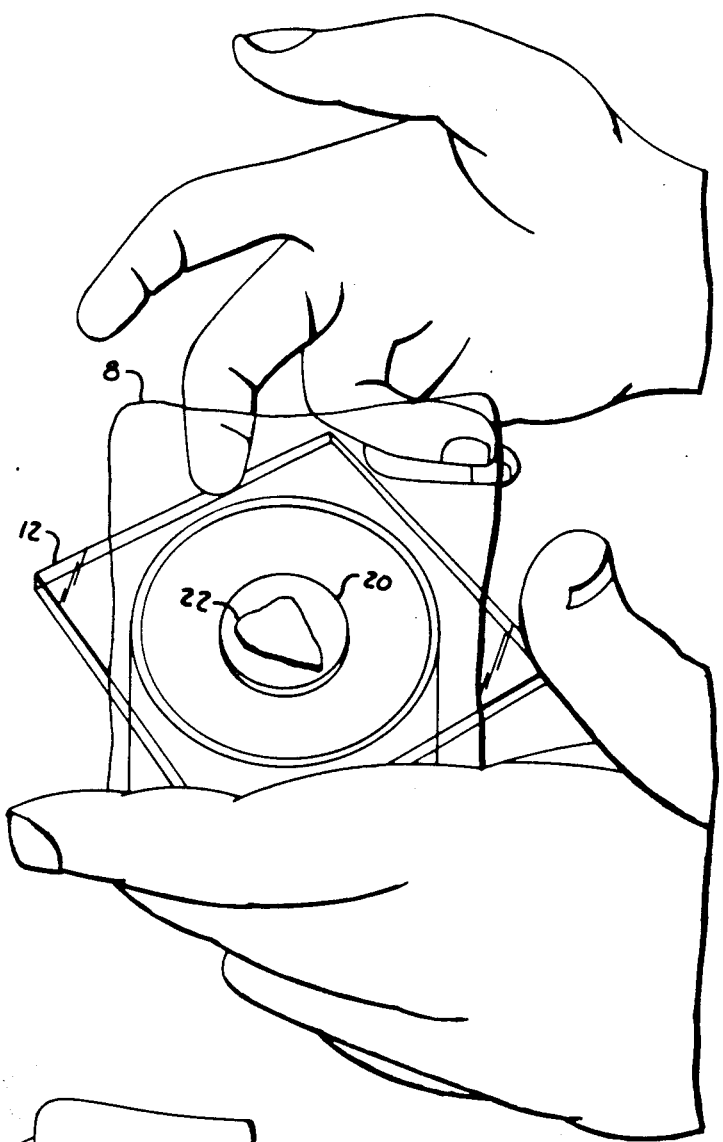
Fig. 4.
Fig. 5.
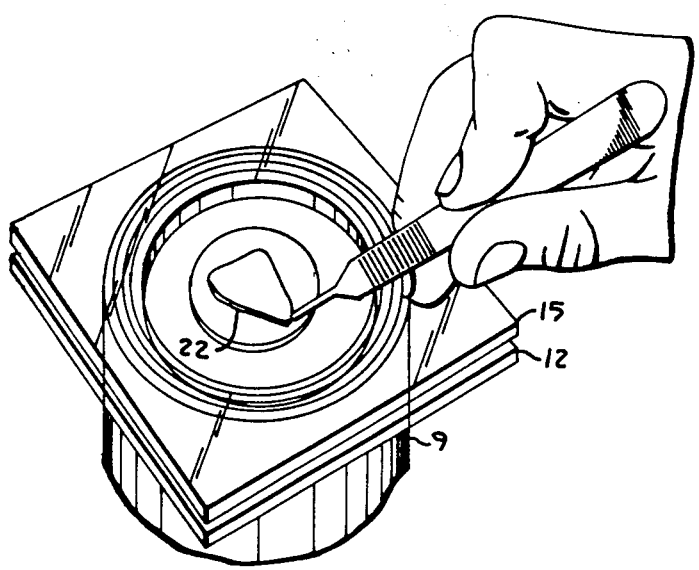

METHOD FOR PREPARING TISSUE SECTIONS

BACKGROUND OF THE INVENTION

This invention relates to the preparation of tissue blocks for sectioning and specifically to preparation for tissue sectioning incidental to the Mohs fresh tissue surgical technique.

In Mohs fresh tissue surgery, cutaneous malignancies and certain major carcinomas of the head and neck are excised using microscopic control. The key to Mohs surgery is the production of high quality, horizontally cut frozen tissue sections, which are subsequently microscopically reviewed to determine whether any residual tumor is present. Initially, the cancerous area is debulked and an amount of tissue is excised. The surgical area has been scored with a scalpel or otherwise mapped for orientation purposes. The scoring will properly orient the surgeon as he or she performs additional excisions as indicated by the results of an inspection of a microscopic section of the excised tissue. Any residual tumor that is indicated by the microscopic inspection is then excised, and the procedure is repeated until all sections are negative. The excised tissue block is generally of curved, or parabolic, cross-section and must be converted to a planar cross section for the cryostatic sectioning. Past techniques have attempted in various ways to obtain a planar section, including freezing of the tissue to a flat polished disc after attempting to roll it flat by use of a scalpel or specially prepared forceps. In the utilization of previous techniques, a technician had to adjust specimen edges that were reluctant to flatten. The manual procedures used were cumbersome and difficult to effect. Typically, they required excellent hand and eye coordination since the specimen was not easily manipulatable.

The tissue block is subsequently inked and sections are cut to a thickness between five and seven micrometers. After staining the section is microscopically examined by the surgeon, who interprets the results on-site, thus saving critical time. Residual neoplasm, if observed in the microscopic section, dictates whether further excision is necessary. This process is repeated until no further tumor is found upon microscopic examination. The Mohs surgery permits the maximum preservation of normal surrounding tissue, and the defect remaining after total cancer removal can be immediately reconstructed.

In order to obtain tissue sections that are satisfactory for microscopic examination through the use of the microtome (also known as a cryostat) the face of the specimen to be sectioned should be planar and parallel to the path of relative movement between the microtome knife and the specimen, thus ensuring sections of uniform thickness suitable for microscopic examination. Preorientation of the mounted tissue so that the planar surface is parallel to the knife path reduces the cutting time involved in that the microtome chuck does not need to be adjusted. The surface presented by the frozen specimen is generally of irregular contour and, using prior techniques, some trimming of the specimen is necessary in order to provide the face of the specimen with a suitable surface. This has been found to be true even when special techniques have been utilized to flatten the peripheral portions of the tissue into plane with the central portion thereof. It is frequently difficult to freeze the specimen to the cryostat disc in an orientation that best presents the tissue block for cutting along the most desirable section. Prior positioning and manipulative techniques have been found to be lacking in terms of ease and reliability of manipulation.

OBJECTS OF THE INVENTION

The principal objects of the present invention are to provide an improved method and apparatus for preparing tissue sections; to provide such a method and apparatus for presenting a tissue block for sectioning by a microtome; to provide such a method and apparatus which precisely orient frozen tissue blocks for sectioning; to provide such a method and apparatus which use a vacuum-retracted membrane to orient the undersurface and peripheral margin of the tissue block for optimum positioning; to provide such a method and apparatus which facilitate manipulation of the tissue block for optimum positioning; to provide such a method and apparatus which are is time-and cost-effective, so as to reduce the overall surgical time necessary to effect the total excision of the malignancy; to provide such a method and apparatus which are relatively simple to use, economical to manufacture, and particularly well adapted for the proposed usage thereof.

Other objects and advantages of this invention will become apparent from the following description taken in conjunction with the accompanying drawings wherein are set forth, by way of illustration and example, certain embodiments of this invention.

SUMMARY OF THE INVENTION

A system for preparing tissue blocks for presentation to a microtome for sectioning is provided. A tissue block, or specimen, is inked and placed on a polished platform, with a tissue surface to be examined against the polished surface. The system is designed to facilitate the rapid production of uniform frozen sections used in Mohs micro controlled fresh tissue surgery.

The platform, with specimen thereon, is placed into a vacuum receptacle assembly and covered by a flexible plastic membrane. The receptacle assembly may be provided with multiple receptacles for receiving multiple platform/specimen complexes for simultaneous processing. The plastic membrane is preferably a polyethylene plastic sheet material and may be fed through a dispenser slot to the operator. A hood, or cover plate, with access means is used to form a seal between the membrane and the vacuum receptacle body. A vacuum source of the vacuum receptacle assembly is activated and evacuates air from between the membrane and the tissue block, flattening the block into a planar unit. At this point, the operator, or surgeon, can manipulate the specimen through the cover plate access means to achieve the most advantageous position on the platform, as determined on a case-by-case basis. Once the tissue block specimen is properly oriented into a flat profile, liquid nitrogen is used to freeze the tissue block to the platform. The liquid nitrogen is swabbed, as with a proctoscopic-type swab, or dripped onto the tissue block for freezing. Alternative means for freezing may be used, including freon.

The membrane is peeled away from the platform and the specimen, and an embedding medium such as O.C.T. compound is applied to the specimen platform and to a mateable corrugated platform. After the O.C.T. compound has partially solidified, the platforms are mated and allowed to solidify. The platforms are subsequently separated, with the tissue block being retained by the corrugated platform, through interaction of the O.C.T. compound and the rough surface of the corrugated platform. Preferably, the specimen platform is provided with an anti-stick formula (such as Teflon-type material) for ease of removal at this stage. The tissue block is now prepared for sectioning and presents a solidly frozen, planar surface for ease of microtome sectioning.

The drawings constitute a part of this specification and include exemplary embodiments of the present invention and illustrate various objects and features thereof.

BRIEF DESCRIPTION OF THE DRAWINGS

FIG. 3 is an enlarged perspective view of the polished platform showing the tissue block specimen in an original position thereon.

FIG. 4 is a schematic representation of one of the preliminary steps according to the present invention.

FIG. 5 is a schematic view of a later step according to the present invention and showing manipulation of the tissue block specimen with the plastic membrane in place.

DETAILED DESCRIPTION OF THE INVENTION

Figure 1:
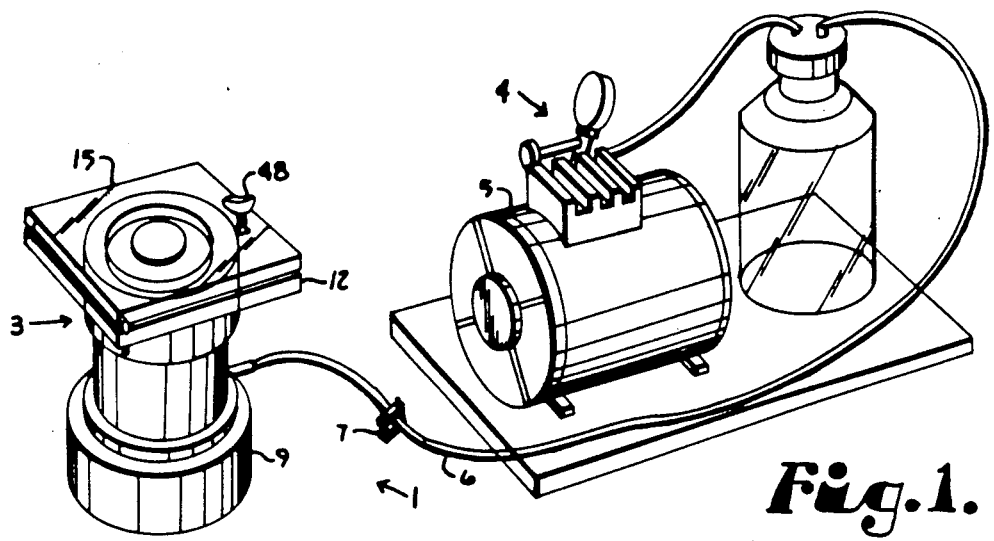
FIG. 1 is a perspective view of an apparatus for preparing tissue sections according to the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, reference numeral 1 generally indicates a retracting and aligning dermal apparatus for preparing tissue sections according to the present invention.

The apparatus 1 includes a vacuum receptacle assembly 3 and a vacuum source 4 as is well-known in the art. The vacuum receptacle assembly 3 is connected to the vacuum source 4, which includes an appropriate vacuum pump 5. A hose 6 operably connects the vacuum source 4 to the vacuum receptacle assembly 3. A clamp 7 is provided to pinch the hose 6 to selectively permit or prevent airflow therethrough. A transparent, flexible membrane 8 is provided for sealing the vacuum receptacle assembly 3 during operation. The receptacle assembly 3 includes a generally cylindrical receptacle structure 9 having an interior chamber 10. The receptacle assembly 3 further includes a baseplate 12 attached to a top portion 13 of the receptacle 9, and a cover plate 15 connected to the baseplate 12 by hinge means. The baseplate 12 and cover plate 15 have respective orifices 17, 18 corresponding in position to the receptacle interior chamber 10 for providing access thereto. Preferably, the baseplate 12 and the cover plate 15 are made of a lucite-type plastic material and are illustrated as such.

A polished disc 20 is provided for receiving a tissue block or specimen 22. As used herein, "polished disc" contemplates a disc having a relatively smooth surface. The polished disc 20 includes a planar, circular polished platform 24 and a central stem 25 depending therefrom. The receptacle assembly includes means for receiving the disc; as illustrated, the baseplate orifice 17 is sized to receive the stem 25 therethrough. The baseplate orifice 17 further includes an elliptical section 26, such that the orifice 17 has a generally "key-hole" shape. This shape facilitates the removal of the disc 20 from the orifice 17, by tipping one edge of the platform 24 into the elliptical section 26 of the orifice 17 and grasping an opposed side of the platform 24. The baseplate 12 includes a recessed step portion 28 surrounding the orifice 17 and sized and recessed sufficiently to receive the polished platform 24 in relatively close fitting relation. A surface 30 of the platform 24 is generally flush with an upper surface 32 of the baseplate 12 when the disc 20 is in position.

Figure 11:
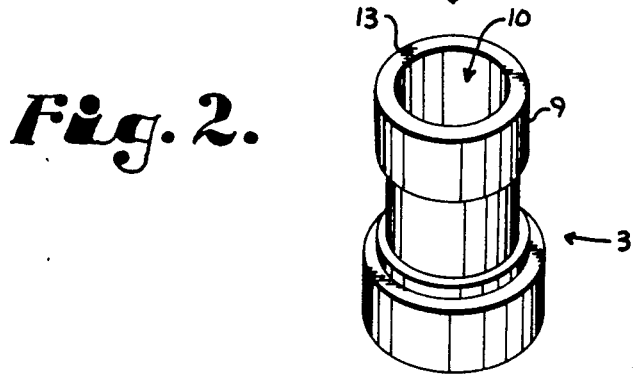
FIG. 11 is an enlarged, fragmentary side elevational view of the vacuum receptacle showing a hinged cover plate thereof in a raised position.

The hinge means swingably connect the cover plate 15 to the baseplate 12, as illustrated in FIG. 11. The hinge means are spring-loaded to perfect a seal between the membrane 8 and the baseplate 12, in the method described below. In order to achieve this result, a good seal must be maintained between the baseplate 12 and the membrane 8 and simultaneously between the membrane 8 and the cover plate 15. An O-ring 35, is arranged in a surrounding position around the cover plate orifice 18. The O-ring 35 is fixed to an under surface 36 of the cover plate 15, but it could be fixed to the baseplate 12. Taken together, the baseplate 12, cover plate 15, and O-ring 35 constitute sealing means for creating a seal between the membrane 8 and the receptacle assembly 3.

Figure 2:
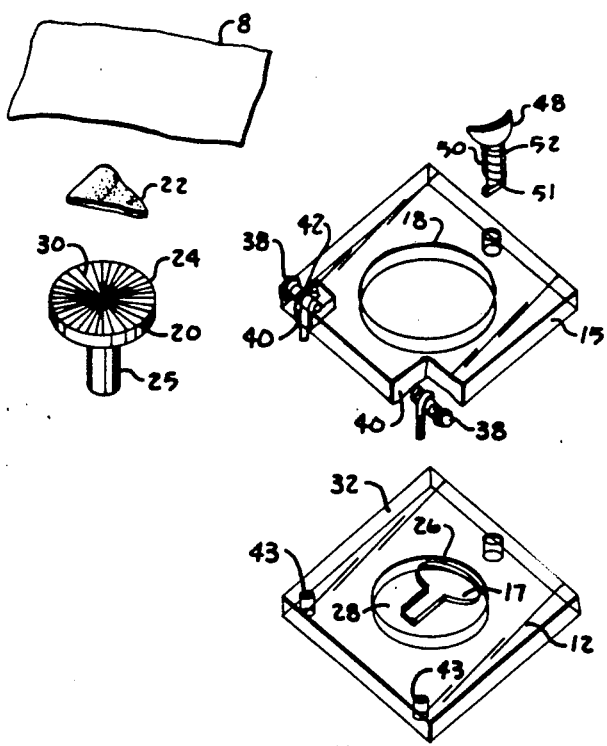
FIG. 2 is an enlarged, exploded view of a vacuum receptacle, polished platform, tissue block specimen, and plastic membrane according to the present invention.

The hinge means include a pair of pivot bolts 38, which extend into the body of the cover plate 15 from opposed sides thereof, as seen in FIG. 2. The pivot bolts 13 extend into slots 40, which are cut into the cover plate 15. The pivot bolts 38 provide means about which spring-loaded bolts 42 swing. The bolts 42 are pivotable about an axis of the pivot bolts 38, extend through respective holes 43 in the baseplate 12 and depend from the baseplate 12. Respective springs 45 are received onto the spring-loaded bolts 42 and held in place by respective nuts 46. The springs 45 tend to bias the cover plate 15 toward the baseplate 12. When the cover plate 15 is in a raised position, as seen in FIG. 11, the spring-loaded bolts 42 will maintain the cover plate 15 in the raised position, allowing the user to position the disc 20.

In a closed, or covering position, the cover plate 15 is generally parallel to the baseplate 12, and the spring-loaded bolts 42 will place an uneven amount of torque on the cover plate 15. To counteract this effect and to further enhance the sealing operation between the base and cover plates 12 and 15, a spring-loaded locking key 48 is provided in a position opposite the bolts 42. The key 48 includes a locking shaft 50 having an oblong locking section 51 thereon. A tension spring 52 is carried on the shaft 50 above the locking section 51, as seen in FIG. 2. The baseplate 12 has an oblong hole therethrough, through which the key 48 can extend. Once the key 48 is inserted through the holes, an approximate 90 degree twist of the key 48 will lock it in place in a spring-loaded manner.

Figure 8:
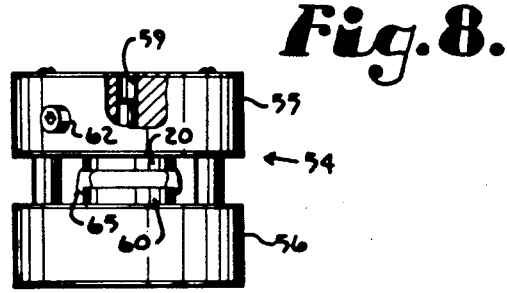
FIG. 8 is a schematic view of two mounting devices for mating the polished and corrugated platforms for transferring the tissue block specimen from the polished platform to the corrugated platform.

A platform mounting device 54 is used in the present method and includes first and second mounting members 55 and 56, which mate one to the other. The first mounting member has alignment bores 57, which matingly receive corresponding alignment spindles 58 of the second mounting member 56. A central bore 59 extends through the first mounting member 55, as seen in FIG. 8. The polished disc stem 25 is receivable into the bore 59, as will be discussed in more detail below. A set screw 62 is provided for locking the stem 25 in the bore 59, and thus the polished disc 20, in position. The second mounting member 56 also includes a central bore (not shown.)

A corrugated disc 60 includes a stem that is receivable into the second mounting member bore for alignment with the polished disc 20.

An alternative corrugated platform 64 may be used instead of the corrugated disc 60, depending on the type of microtome or cryostat being utilized in the examination process.

The basic apparatus 1 having been described, the method according to the present invention will now be discussed in detail, with further structural details also being added. The present method utilizes a vacuum-retracted membrane to orient the under surface and peripheral margin of various tissue specimens, including mucosa, dermis, and cartilage.

FIG. 3 represents an initial step in the present method, wherein the tissue specimen 22 to be examined using horizontal frozen sections per the Mohs technique has been placed onto the polished disc 20. Deep margins of the tissue specimen 22 are inked in the standard Mohs fashion. The inked specimen 22 is placed onto the polished platform 24 such that the surface to be examined for margins is directly against the polished surface. As illustrated, the surface 30 of the platform 24 has been lightly scored radially and has an anti-stick coating thereon such as Teflon-type material. The score lines assist in retracting the plastic membrane, as the score lines allow flow of air across the surface 30. The use of the anti-stick coating obviates the need to apply an anti-stick lubricant, which may be unevenly applied, subsequently resulting in improper release of the specimen 22. The disc 20, with tissue specimen 22 thereon, is then placed into the receptacle structure 9. Specifically, the stem 25 is inserted through the orifice 17, generally in the center of the baseplate step portion 28. The platform 24 is received into the step portion 28, which is sized to receive the platform 24 in close relationship. However, there is sufficient clearance for air movement into the receptacle chamber 10.

FIG. 4 shows the polished disc 20 in place on the baseplate 12, with the tissue block 22 carried on the platform 24. FIG. 4 further represents the membrane 8 being placed over the platform 24 and tissue specimen 22, covering same and extending outwardly therefrom. It is important to ensure that the borders of the membrane 8 extend beyond the seal area of the baseplate 12 covered by the O-ring 35 when the cover plate 15 is brought into contact with the baseplate 12. If the membrane does not extend beyond the O-ring seal area, a faulty seal will result and a new membrane 8 will be necessary.

With the membrane 8 in place, the cover plate 15 is brought into its covering position over the baseplate 12, as seen in FIG. 5. The key 48 is pushed through the corresponding hole in the baseplate 12 and rotated into a locking position. The tissue specimen 22 is inspected to ensure that the desired orientation has not been disturbed during placement of the membrane 8 and securing of the cover plate 15.

The operator then ensures that the clamp 7 is closed and activates the vacuum pump 5. It is envisioned that an alternative foot switching valve or the like may be provided in place of the clamp 7 to regulate the vacuum source 4. The clamp 7 is slowly opened, which allows the vacuum source 4 to draw air from the vacuum receptacle assembly 3, retracting the membrane 8 onto the platform 24. This retraction pulls the edges of the tissue specimen 22 down into a planar orientation parallel to the platform 24. The tissue specimen 22 can then be manipulated by the operator (generally the surgeon), as seen in FIG. 5. Either a medical instrument, as seen in FIG. 5, or the operator's fingers may be used to manipulate the specimen through the membrane until a desired orientation of the tissue specimen 22 is obtained. This manipulation is done while gradually reaching full vacuum of approximately 30 cm $H_2O$. Upon complete evacuation of the receptacle chamber 10, and the manipulation through the membrane 8, the peripheral edges of the tissue specimen are oriented properly for subsequent tissue sectioning.

The operator should observe ink flow patterns and occlude any running ink streams with the medical instrument or finger. If the peripheral border does not flatten completely, the specimen 22 can be gently secured with the operator's fingers as the edges are gently pressed down to create additional vacuum streams, which will further flatten the edge down.

In the event that the tissue specimen 22 cannot be properly oriented, a new membrane 8 is used and the securing and evacuating steps are repeated. If this is necessary, the membrane should be lifted from side to side at an approximate 30 degree angle to the platform, and a cotton swab used to hold the specimen 22 in place by a transmembrane approach. It is noted that the use of sharp instruments or long fingernails must be avoided during the membrane/specimen manipulation to ensure against leaks. If a leak does occur, the membrane 8 is replaced with a substitute membrane 8. It is also necessary to avoid allowing the specimens to become inflexible due to drying.

In the event that a vacuum receptacle assembly that can accommodate more than one disc 20 is used, it has been found that all of the discs 20 should be in place during the vacuum evacuation, even if not all have tissue specimens thereon.

Figure 6:
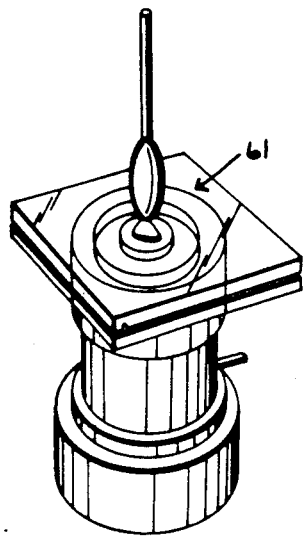
FIG. 6 is a schematic view showing a later step according to the present invention wherein the tissue block specimen is being frozen.

In FIG. 6, the vacuum alignment and orientation step has been completed and solidification of the tissue specimen 22 is now accomplished. As illustrated, a large swab with liquid nitrogen thereon is used to freeze the tissue specimen 22 to the platform 24. It has been found that proctoscopic-type swabs work well. Freon and other types of freezing agents may also be used, but the freeze is generally less satisfactory than that obtained using the liquid nitrogen.

A frozen polished disc/specimen complex 61 is now removed from the vacuum receptacle assembly 3. The cover plate is released by disengaging the locking key 48 and raised into the upright position. The membrane 8 is grasped and peeled from the specimen 22 at an angle of approximately five to ten degrees from horizontal. If this angle is increased, it has been found that the tissue specimen 22 may separate from the platform 24. After the membrane 8 is removed, the disc/specimen complex 61 is removed by tipping one side of the platform 24 into the larger portion of orifice 17 and grasping the opposed side. In the event that the disc 20 is frozen in place, a prying device may be used. The disc/specimen complex 61 is immediately placed into the first mounting member 55 for further processing.

The platform mounting device 54 is kept at a constant temperature of around −25° C. The corrugated disc 60 is placed into the second mounting member 56 and an amount of O.C.T. compound 65 is placed thereon. O.C.T. compound 65 is an embedding medium for frozen tissue specimens that is well-known in the art. O.C.T. is an abbreviation for "Optimum Cutting Time". O.C.T. compound is sold under the mark TISSUE TEK II by Miles Scientific, a Division of Miles Laboratories.

Figure 7:
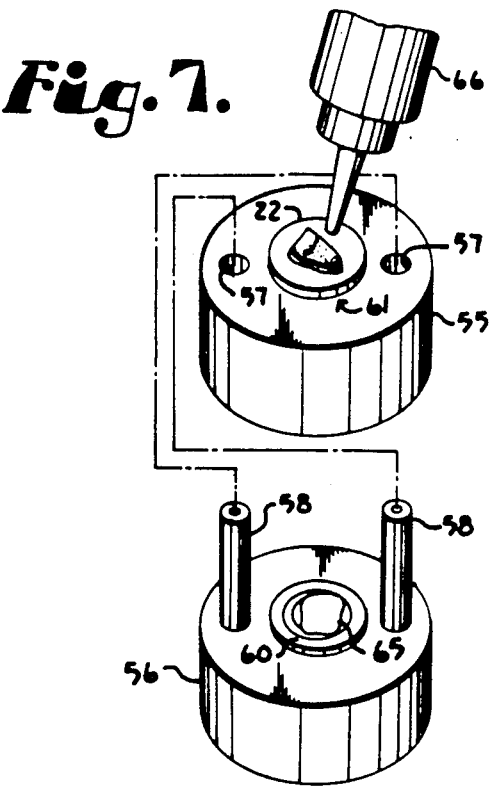
FIG. 7 is an exploded schematic view of a later step according to the present invention for transferring the tissue block specimen from the polished platform to a corrugated platform.
Figure 9:
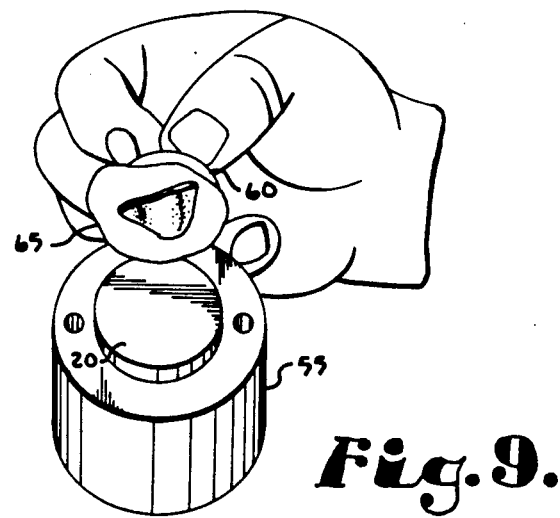
FIG. 9 represents a final step according to the present invention wherein the tissue block specimen has been transferred to the corrugated platform and is embedded in a cutting compound.

The O.C.T. compound 65 is also applied to the polished disc 20 by means of a bottle 66, as illustrated in FIG. 7, which also shows that O.C.T. compound 65 has been applied to the corrugated disc 60. The polished disc 20 is secured into the first mounting member by means of tightening the set screw 62 against the stem 25. The O.C.T. compound 65 is allowed to partially solidify, and the first mounting member is inverted and received onto the second mounting member alignment spindles 58, with an exposed surface of the tissue specimen 22 embedded in the O.C.T. compound 65, as seen in FIG. 8. The extremely cold mated platform mounting device 54 is kept in the position shown in FIG. 8 for a time sufficient to allow the O.C.T. compound 65 to solidify. The two mounting members 55 and 56 are subsequently separated, leaving the corrugated disc 60 frozen to the tissue specimen 22. The polished disc 20 is retained in the first mounting member 55 by means of the set screw 62. As seen in FIG. 9, the operator can remove the corrugated disc 60 by pulling it away from the polished disc 20. Since the polished disc 20 is smooth and coated with an anti-stick material, the O.C.T. compound 65 adheres to the corrugated disc 60 and is removed with it. The O.C.T. compound 65 will carry the embedded tissue specimen 22 with it, which presents a smooth, planar surface ready for processing in a microtome to produce uniform frozen sections for use in Mohs microscopically controlled surgery.

If the polished disc/specimen-O.C.T. compound/corrugated disc complex fails to separate easily, the polished disc stem 25 may be placed into a heat source, which will enable it to be removed.

Figure 10:
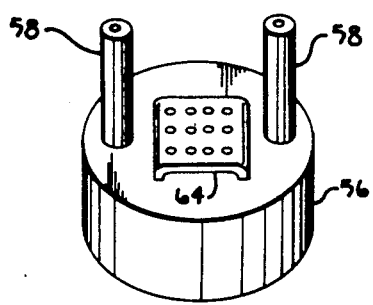
FIG. 10 is a perspective view of an alternative type mounting platform.

FIG. 10 represents the use of an alternative corrugated platform 64, which may be substituted in the noted method for the corrugated disc 60 and is designed to be used with a different type of cryostat.

It is to be understood that while certain forms of the present invention have been illustrated and described herein, it is not to be limited to the specific forms or arrangement of parts described and shown.

What is claimed and desired to be secured by Letters Patent is as follows:

1. A method for preparing a tissue specimen for sectioning in a microtome or the like; said method comprising:
    (a) positioning said tissue specimen on a polished disc with an undersurface of said tissue specimen to be examined contacting a surface of said disc;
    (b) placing said polished disc in a receptacle structure;
    (c) covering said polished disc and said tissue specimen with a membrane;
    (d) sealing said membrane relative to said receptacle structure and over said polished disc and said tissue specimen;
    (e) drawing air from said receptacle structure in such a manner as to retract said membrane toward said receptacle structure, thereby tending to flatten an undersurface of said tissue specimen;
    (f) manipulating said tissue specimen to a desired orientation on said polished disc;
    (g) freezing said tissue specimen onto said polished disc;
    (h) removing said membrane from a polished disc/tissue specimen complex formed by the freezing of said tissue specimen to said polished disc;
    (i) applying an embedding medium to said polished disc/tissue specimen complex;
    (j) mating said polished disc/tissue specimen complex with a corrugated disc having an embedding medium thereon; and
    (k) disengaging said polished disc from said tissue specimen, which is retained by said embedding medium and said corrugated disc, whereby said tissue specimen undersurface presents a generally planar surface for sectioning.

2. The method as set forth in claim 1 wherein said step of covering said polished disc and said tissue specimen includes covering with a flexible, plastic membrane that extends radially from a periphery of said polished disc; and wherein said step of sealing said plastic membrane relative to said receptacle structure includes placing an O-ring device over said membrane in a surrounding position around said disc and maintaining pressure against said O-ring to seal said membrane relative to said receptacle structure.

3. The method as set forth in claim 1 wherein said step of placing said polished disc in a receptacle structure includes placing said disc on a baseplate attached to said receptacle structure; said baseplate having an orifice for providing air communication with an interior chamber of said receptacle structure; and wherein said step of sealing said membrane relative to said receptacle structure includes surrounding said disc with a cover plate having an orifice therein positioned above said disc and maintaining said cover plate in tight contact with said membrane and said baseplate.

* * * * *